United States Patent
Liu et al.

(10) Patent No.: US 7,059,196 B1
(45) Date of Patent: Jun. 13, 2006

(54) DISPOSABLE WIRELESS PRESSURE SENSOR

(75) Inventors: James Z. Liu, Rockford, IL (US); James D. Cook, Freeport, IL (US); Peter P. Dierauer, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 31 days.

(21) Appl. No.: 10/995,460

(22) Filed: Nov. 22, 2004

(51) Int. Cl.
*H01L 41/08* (2006.01)

(52) U.S. Cl. .................................... 73/754; 310/313

(58) Field of Classification Search ............ 73/754, 73/721, 727; 310/313
See application file for complete search history.

(56) References Cited

U.S. PATENT DOCUMENTS

| | | | |
|---|---|---|---|
| 3,931,446 A | 1/1976 | Murayama et al. | 428/421 |
| 4,600,855 A | 7/1986 | Strachan | 310/338 |
| 5,675,314 A * | 10/1997 | Chaklader | 340/443 |
| 5,821,425 A * | 10/1998 | Mariani et al. | 73/703 |
| 6,144,288 A * | 11/2000 | Jahn et al. | 340/10.33 |
| 6,293,136 B1 * | 9/2001 | Kim | 73/19.03 |
| 6,301,973 B1 | 10/2001 | Smith | 73/861.357 |
| 6,475,170 B1 | 11/2002 | Doron et al. | 600/587 |
| 6,486,588 B1 | 11/2002 | Doron et al. | 310/322 |
| 6,504,286 B1 | 1/2003 | Porat et al. | 310/324 |
| 6,640,613 B1 * | 11/2003 | Rapp et al. | 73/24.01 |
| 6,670,739 B1 * | 12/2003 | Horiuchi et al. | 310/313 R |
| 6,681,623 B1 | 1/2004 | Bonne et al. | 73/202 |
| 6,953,977 B1 * | 10/2005 | Mlcak et al. | 257/414 |
| 6,958,565 B1 * | 10/2005 | Liu | 310/313 R |
| 2003/0107454 A1 * | 6/2003 | Nakamura et al. | 333/133 |
| 2005/0225200 A1 * | 10/2005 | Liu | 310/313 R |

\* cited by examiner

*Primary Examiner*—Edward Lefkowitz
*Assistant Examiner*—Andre Allen
(74) *Attorney, Agent, or Firm*—Kermit D. Lopez; Luis M. Ortiz

(57) ABSTRACT

In general, a dielectric polymer substrate provided and an antenna formed upon the dielectric polymer substrate. A piezoelectric polymer layer (e.g., a polyvinylidene fluoride (PVDF) piezoelectric film) can be formed above the dielectric polymer substrate. Additionally, an interdigital (IDT) layer can be configured upon the PVDF piezoelectric layer, thereby permitting the piezoelectric polymer layer and the IDT layer to detect pressure data and transmit the data to a receiver via the antenna.

18 Claims, 2 Drawing Sheets

DISPOSABLE WIRELESS PRESSURE SENSOR

TECHNICAL FIELD

Embodiments are generally related to sensing devices and applications. Embodiments are also related to pressure sensor devices, systems and methods thereof. Embodiments are additionally related to disposable sensing devices based on piezoelectric polymer film materials. Embodiments are additionally related to medical devices for sensing bodily pressure based on fluid within a conduit.

BACKGROUND OF THE INVENTION

A variety of sensors can be utilized to detect conditions, such as pressure and temperature. The ability to detect pressure and/or temperature is an advantage to any device exposed to variable pressure conditions, which can be severely affected by these conditions. An example of such a device is a catheter, which of course, can experience variations in both temperature and pressure. Many different techniques have been proposed for sensing the pressure and/or temperature in catheters, and for delivering this information to an operator so that he or she is aware of pressure and temperature conditions associated with a catheter and any fluid, such as blood flowing therein.

One type of sensor that has found wide use in pressure and temperature sensing applications is the Surface Acoustic Wave (SAW) sensor, which can be composed of a sense element on a base and pressure transducer sensor diaphragm that is part of the cover. For a SAW sensor to function properly, the sensor diaphragm should generally be located in intimate contact with the sense element at all pressure levels and temperatures.

One of the problems with current SAW sensor designs, particularly those designs adapted to delicate pressure and temperature sensing applications, is the inability of conventional SAW sensing systems to meet the demand in low pressure applications. (e.g., 0 to 500 mmHg), while doing so in an efficient and low cost manner. Such systems are inherently expensive, awkward, and often are not reliable in accurately sensing air pressure and temperature. There is a continuing need to lower the cost of SAW sensor designs utilized in pressure and/or temperature sensing applications, particularly wireless pressure sensors.

To lower the cost and raise efficiency, few components, less expensive materials and fewer manufacturing-processing steps are necessary. In order to achieve these goals, it is believed that a disposable SAW pressure sensor made of polymer substrate should be implemented, along with low cost processing steps. To date, such components have not been adequately achieved.

One area where the ability to detect pressure and/or temperature is critically important is in the field of medical applications. Pressure within a conduit, for example, such as a catheter, can be measured utilizing a number of techniques. Perhaps the most common device for such measurement is a mechanical gauge, which can be coupled through one wall of the conduit to the fluid pressure within the conduit. Inside the gauge, a needle is deflected over a scale in proportion to the pressure within the conduit. In some instances, the standard pressure gauge may be replaced with a transducer, which converts pressure into an electrical signal, which is then monitored. One important medical application for a pressure sensor involves detecting a patient's blood pressure, and/or intracranial pressure.

One typical method of monitoring blood pressure is to measure the fluid pressure within an intravenous tube, which is hydraulically coupled to the patient's vein. A catheter is inserted into the patient's vein and a plastic tube or conduit coupled to the catheter. A saline solution can be drip-fed through the plastic tubing or conduit to maintain a pressure balance against the pressure within the patient's vein. The saline fluid acts as a hydraulic fluid to cause the pressure within the plastic tubing to correspond to the pressure within the patient's vein. Hence, by measuring the fluid pressure within the tubing, the patient's blood pressure will be known.

Various conventional SAW sensing devices are capable of measuring blood pressure. Such devices typically are configured from ceramic materials (like PZT), quartz-type piezoelectric materials or lithium niobate. Such devices are disadvantageous for medical applications, because the above-referenced materials utilized by such devices are inherently self-resonant, having extremely low piezoelectric coupling coefficient, expensive and difficult for micro-machining, and consequently, grossly reduce the possibility of making a low cost pressure sensor for medical applications.

Conventional quartz-based SAW pressure sensors are also expensive to implement in medical applications, rendering their widespread use limited. Micro-machining in quartz is nothing close to that of silicon. It is therefore believed that a solution to such problems involves a disposable low cost sensor packaging system, particularly one that is suited to medical applications.

BRIEF SUMMARY

The following summary is provided to facilitate an understanding of some of the innovative features unique to the embodiments disclosed herein and is not intended to be a full description. A full appreciation of the various aspects of the embodiments discussed herein can be gained by taking the entire specification, claims, drawings, and abstract as a whole.

It is, therefore, one aspect of the present invention to provide for improved sensing devices and applications It is another aspect of the present invention to provide for improved pressure sensor devices, systems and methods thereof.

It is a further aspect of the present invention to provide for an improved disposable wireless pressure sensor.

It is an additional aspect of the present invention to provide for a pressure sensor system based on interdigital transducer (IDT) and polymer piezoelectric materials.

The aforementioned aspects of the invention and other objectives and advantages can now be achieved as described herein. Disposable sensor systems and method are disclosed. In general, a dielectric polymer substrate provided and a microstrip antenna formed upon the dielectric polymer substrate. A piezoelectric polymer layer (e.g., a polyvinylidene fluoride (PVDF) piezoelectric film) and the microstrip antenna can be formed flexible in nature, which makes them suitable for conformal wraparound designs and applications. Additionally, an interdigital (IDT) layer can be configured upon the PVDF piezoelectric layer, thereby permitting the piezoelectric polymer layer and the IDT layer to detect pressure data and transmit the data to a receiver via the antenna.

A first bonding layer can be formed between the dielectric polymer substrate and the piezoelectric polymer layer. Also, a second bonding layer can be formed between the IDT layer and the piezoelectric polymer layer. A protective cover layer can also be configured above the IDT layer. The IDT layer can be formed as a plurality of IDT finger electrodes, which may be configured from copper. Additionally, the polymer substrate can include a gap formed centrally therein, such that the gap is filled with a gel comprising a low thermal conductivity and bio-compatible material. The polymer substrate is generally formed from a low thermal conductivity dielectric substrate material.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate at least one embodiment of the present invention and are not intended to limit the scope of the invention.

Figure 1:
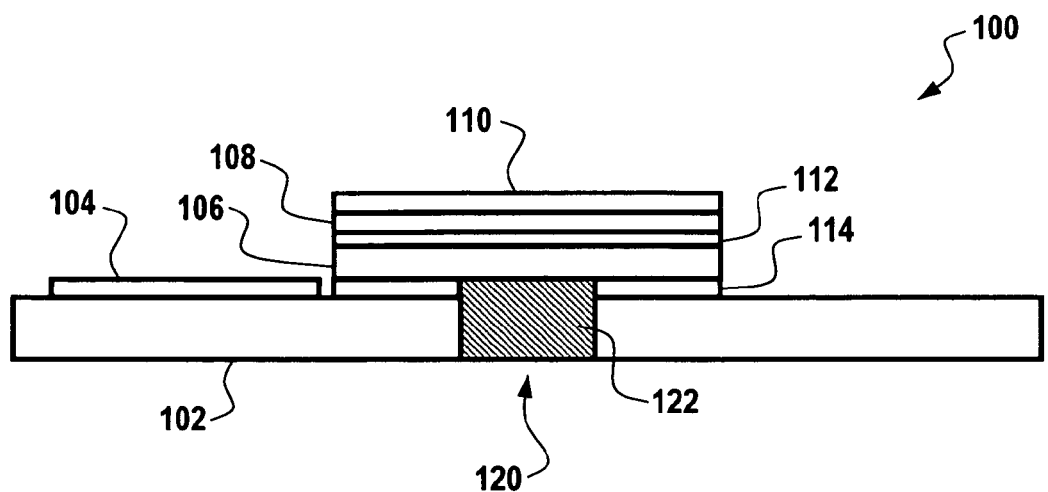
FIG. 1 illustrates a side view of a disposable wireless pressure sensor system, which can be implemented in accordance with a preferred embodiment.
Figure 2:
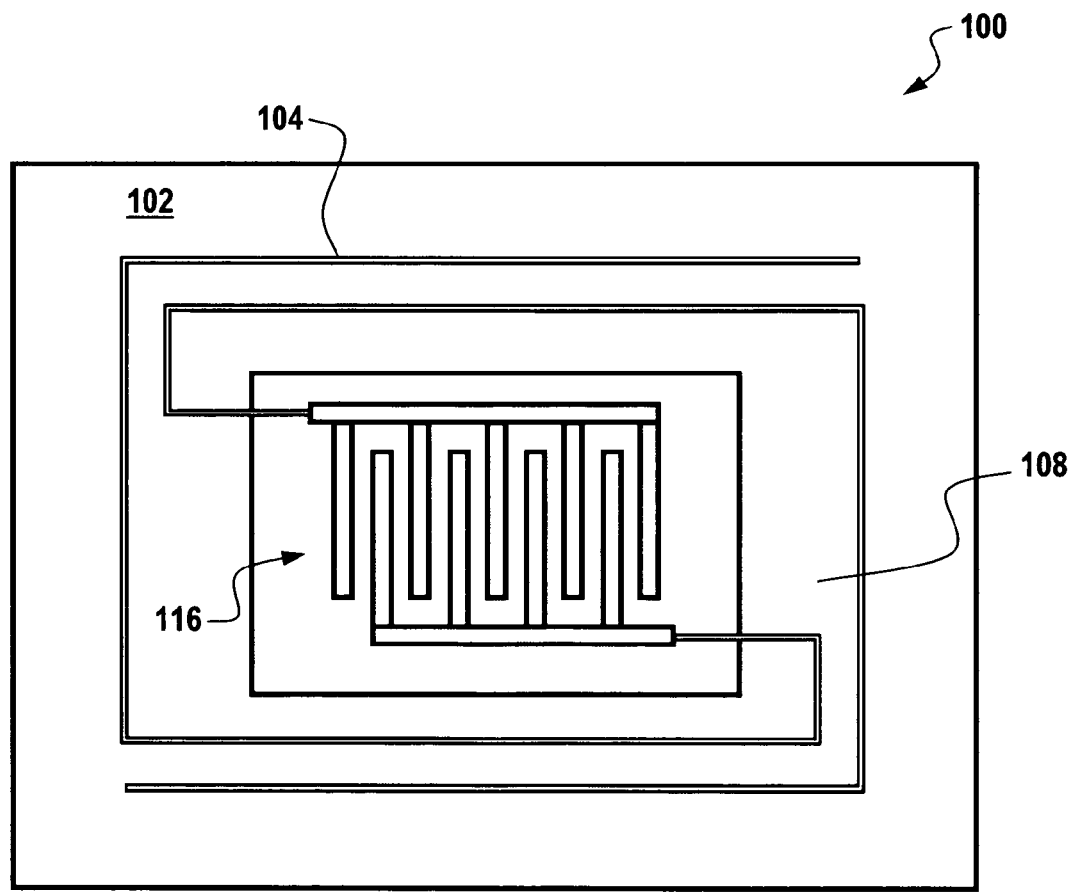
FIG. 2 illustrates a top view of the disposable wireless pressure sensor system depicted in FIG. 1, in accordance with a preferred embodiment.

FIG. 1 illustrates a side view of a disposable wireless pressure sensor system 100, which can be implemented in accordance with a preferred embodiment. FIG. 2 illustrates a top view of the disposable wireless pressure sensor system 100 depicted in FIG. 1, in accordance with a preferred embodiment. Note that in FIGS. 1–2, identical or similar parts are generally indicated by identical reference numerals. System 100 generally includes a dielectric polymer substrate 102.

A microstrip antenna 104 can be formed upon the dielectric polymer substrate 102. Additionally, a piezoelectric polymer layer 106 can be formed above the dielectric polymer substrate, while an interdigital (IDT) layer 108 can be configured upon the piezoelectric polymer layer 106, thereby permitting the piezoelectric polymer layer 106 and the IDT layer 108 to detect pressure data and transmit the data to a receiver utilizing the antenna 104. The piezoelectric polymer layer 106 can be configured as a thin sheet having a thickness in a range of 10–20 microns, depending upon design considerations.

Additionally, a first bonding layer 114 can be formed between the dielectric polymer substrate 102 and the piezoelectric polymer layer 106. A second bonding layer 112 can be formed between the IDT layer 108 and the piezoelectric polymer layer 106. First and second bonding layers 114 and 112 function as adhesives. The adhesive material for bonding layers 114, 112 can be, for example, cyano-acrylate or a similar material. The adhesive or bonding layer thickness for layers 114, 112 can be in a range of approximately 10 to 20 micrometers depending of course upon design considerations.

A protective cover layer 110 can be formed above the IDT layer. The protective cover layer 110 can be formed as a protective plastic sheet in order to ensure mechanical and chemical protection of system 100 as a whole. The IDT layer 108 can be configured to include IDT finger electrodes 116, which are depicted in FIG. 2. Each of the IDT finger electrodes 116 can be formed from copper. The copper IDT thickness can be for example, in a range of approximately 25 micrometers to 125 micrometers, depending upon design considerations. Note that in order to provide lower frequency capabilities, a winder line width, along with bigger device sizes thereof, the IDT finger electrodes can be printed on the piezoelectric polymer layer 106, or can be electroplated or etched form a large sheet of IDT finger electrodes thereof.

The dielectric polymer substrate 102 can also be configured to include a gap 120 filled with a gel 122 formed from a low thermal conductivity and biocompatible material. The piezoelectric polymer layer 106 can be configured as a polyvinylidene fluoride (PVDF) piezoelectric film, while the dielectric polymer substrate 102 can be formed from a low thermal conductivity dielectric substrate material. It is believed that the use of PVDF piezoelectric film in accordance with the preferred embodiment described herein can result in substantial cost-savings and increased sensor efficiency, particularly in medical pressure sensing applications.

One example where system 100 can be particularly useful is the field of medical applications, such as blood pressure sensing. The PVDF piezoelectric film is therefore formed on the biocompatible low thermal conductivity dielectric polymer substrate 102. The PVDF piezoelectric film changes with temperature and pressure. Utilizing a low thermal conductivity substrate, for example, the pyroelectric change by blood can be minimized. The antenna 104 can be printed on the dielectric polymer substrate. Thus, in accordance with the preferred embodiment described herein, a number of transceivers can be provided including a piezoelectric polymer sheet material, which is less costly and much easier to work with than conventional pressure sensing devices.

Figure 3:
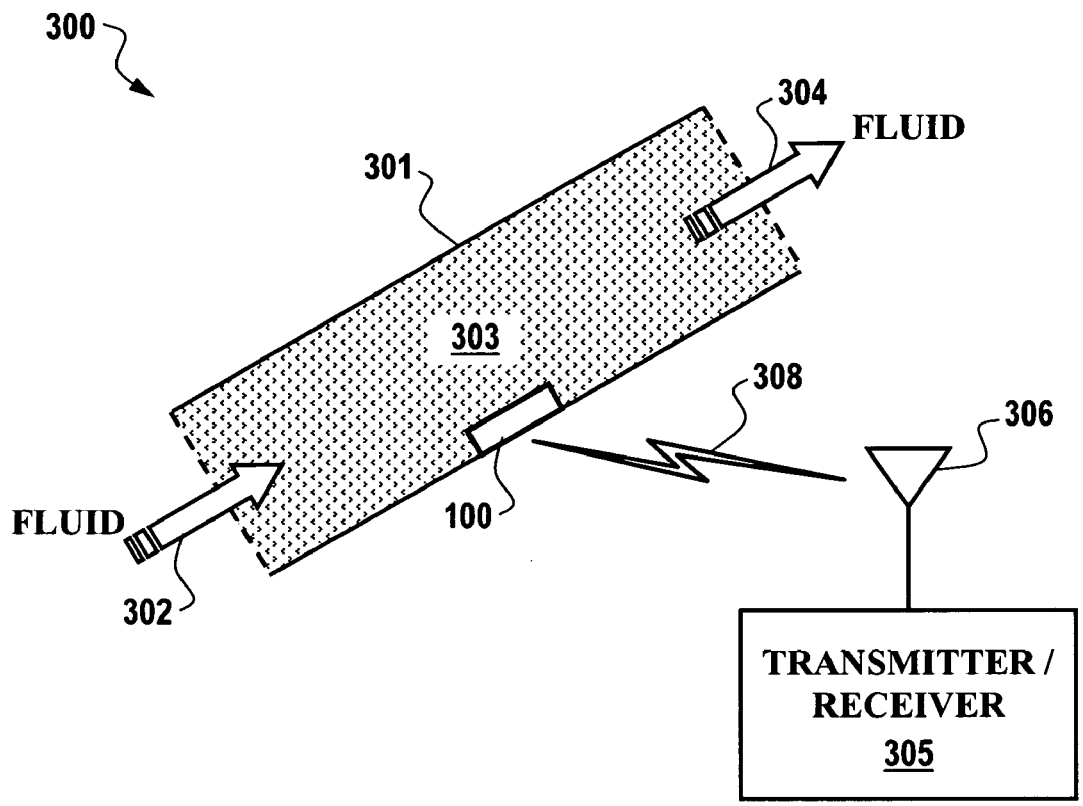
FIG. 3 illustrates a schematic diagram of a medical pressure sensing system, which can be implemented in accordance with an alternative embodiment.

FIG. 3 illustrates a schematic diagram of a medical pressure sensing system 300, which can be implemented in accordance with an alternative embodiment. Note that in FIGS. 1–3, identical or similar parts or components are generally indicated by identical reference numerals. Thus, sensor or system 100 of FIG. 1 is also depicted in FIG. 3 at a location relative to a conduit 301, which can be implemented as, for example, a catheter through which fluid 303 flow, as indicated by arrows 302 and 304. Fluid 303 can be, for example, blood. System or sensor 100 can therefore transmit and receive data to and from a transmitter/receiver 304, which includes an antenna 306. The wireless transmission of such data is indicated in FIG. 3 by arrows 308. System 300 can therefore be utilized for measuring bodily fluid pressure within conduit 301.

Figure 4:
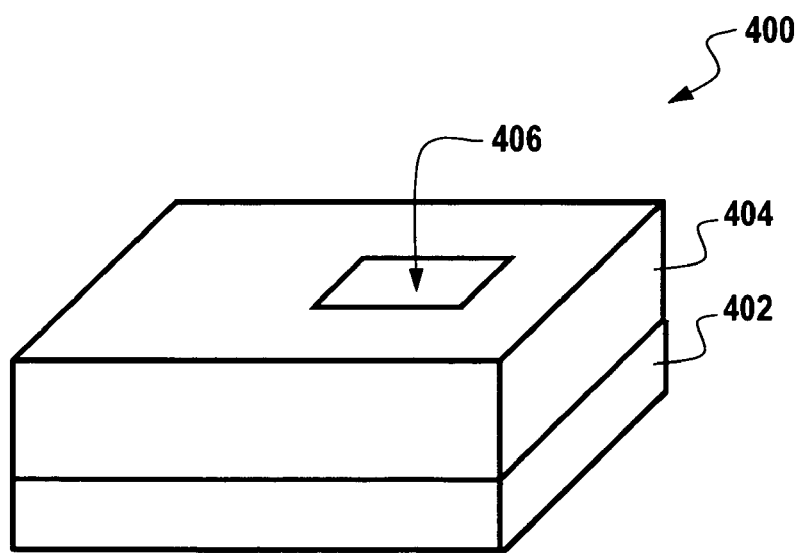
FIG. 4 illustrates a schematic diagram of a microstrip antenna, which can be implemented in accordance with a preferred embodiment.

FIG. 4 illustrates a schematic diagram of a microstrip antenna 400, which can be implemented in accordance with a preferred embodiment. Microstrip antenna 400 generally includes a dielectric substrate 404 located above a ground plane 402. A radiating patch 406 is generally disposed on or in substrate 404. Note that microstrip antenna 400 of FIG. 4 is analogous to microstrip antenna 104 of FIG. 1. For example, microstrip antenna 104 can be formed upon a dielectric polymer substrate 102 as indicated in FIG. 1. Thus, substrate 102 of FIG. 1 is similar to substrate 404 of FIG. 4.

Because a dielectric polymer substrate, such as substrate 404 can be flexible, the configuration of microstrip antenna 400 is suitable for adaptation to conformal wrap-around type designs and applications. Microstrip antennas, such as antenna 400, offer a number of advantages compared to conventional microwave antennas such as, for example light weight, low volume, and thin profile configurations, which can be made conformal; low fabrication cost; and readily amendable to mass production. Linear and circular polarizations are also possible with simple feed configurations. Additionally, dual-frequency and dual-polarization antennas can be easily constructed; because, no cavity backing is required and such devices can be easily integrated with microwave circuits.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

Having thus described the invention what is claimed is:

1. A disposable sensor system, comprising:
a dielectric polymer substrate and an antenna formed upon said dielectric polymer substrate;
a piezoelectric polymer layer formed above said dielectric polymer substrate; and
an interdigital (IDT) layer formed upon said piezoelectric polymer layer, thereby permitting said piezoelectric polymer layer and said IDT layer to detect pressure data and transmit said data to a receiver utilizing said antenna wherein said dielectric polymer substrate comprises a gap formed centrally therein, wherein said gap is filled with a gel comprising a low thermal conductivity and biocompatible material.

2. The system of claim 1 further comprising:
a bonding layer formed between said dielectric polymer substrate and said piezoelectric polymer layer.

3. The system of claim 1 further comprising:
a bonding layer formed between said IDT layer and said piezoelectric polymer layer.

4. The system of claim 1 further comprising a protective cover layer formed above said IDT layer.

5. The system of claim 1 wherein said IDT layer comprises a plurality of IDT finger electrodes.

6. The system of claim 5 wherein each of said IDT finger electrodes among said plurality of IDT finger electrodes comprise copper.

7. The system of claim 1 wherein said piezoelectric polymer layer comprises a polyvinylidene fluoride (PVDF) piezoelectric film.

8. The system of claim 1 wherein said dielectric polymer substrate comprises a low thermal conductivity dielectric substrate material.

9. The system of claim 1 wherein said antenna is printed on said dielectric polymer substrate.

10. A disposable sensor system, comprising:
a dielectric polymer substrate and an antenna formed upon said dielectric polymer substrate, wherein said dielectric polymer substrate comprises a low thermal conductivity dielectric substrate material;
a piezoelectric polymer layer formed above said dielectric polymer substrate, said dielectric polymer substrate comprises a gap formed centrally therein, wherein said gap is filled with a gel comprising a low thermal conductivity and bio-compatible material and wherein said piezoelectric polymer layer comprises a polyvinylidene fluoride (PVDF) piezoelectric film;
an interdigital (IDT) layer formed upon said piezoelectric polymer layer, wherein said IDT layer comprises a plurality of IDT finger electrodes;
a protective cover layer formed above said IDT layer;
a first bonding layer formed between said dielectric polymer substrate and said piezoelectric polymer layer; and
a second bonding layer formed between said IDT layer and said piezoelectric polymer layer, thereby permitting said piezoelectric polymer layer and said IDT layer to detect pressure data and transmit said data to a receiver utilizing said antenna.

11. A disposable sensor method, comprising the steps:
forming an antenna upon a dielectric polymer substrate;
configuring a piezoelectric polymer layer above said dielectric polymer substrate; and
locating an interdigital (IDT) layer upon said piezoelectric polymer layer, thereby permitting said piezoelectric polymer layer and said IDT layer to detect pressure data and transmit said data to a receiver utilizing said antenna forming a gap from centrally form said dielectric polymer substrate; and filling said gap with a gel comprising a low thermal conductivity and biocompatible material.

12. The method of claim 11 further comprising the step of forming a bonding layer between said dielectric polymer substrate and said piezoelectric polymer layer.

13. The method of claim 11 further comprising the step of forming a bonding layer between said IDT layer and said piezoelectric polymer layer.

14. The method of claim 11 further comprising the step of forming a protective cover layer above said IDT layer.

15. The method of claim 11 further comprising the step of configuring said IDT layer to comprise a plurality of IDT finger electrodes comprising copper.

16. The method of claim 11 further comprising the step of configuring said piezoelectric polymer layer as a polyvinylidene fluoride (PVDF) piezoelectric film.

17. The method of claim 11 further comprising the step of configuring said dielectric polymer substrate from a low thermal conductivity dielectric substrate material.

18. The method of claim 11 wherein the step of forming said antenna upon said dielectric polymer substrate further comprises the step of printing said antenna on said dielectric polymer substrate.

* * * * *